(12) United States Patent
Buck

(10) Patent No.: US 6,258,548 B1
(45) Date of Patent: Jul. 10, 2001

(54) SINGLE OR MULTIPLE ANALYTE SEMI-QUANTITATIVE/QUANTITATIVE RAPID DIAGNOSTIC LATERAL FLOW TEST SYSTEM FOR LARGE MOLECULES

(75) Inventor: Robert L. Buck, Sherwood, OR (US)

(73) Assignee: A-Fem Medical Corporation, Portland, OR (US)

(*) Notice: Subject to any disclaimer, the term of this patent is extended or adjusted under 35 U.S.C. 154(b) by 0 days.

(21) Appl. No.: 09/092,191

(22) Filed: Jun. 5, 1998

Related U.S. Application Data

(60) Provisional application No. 60/048,902, filed on Jun. 5, 1997.

(51) Int. Cl.[7] ................................................. G01N 33/558
(52) U.S. Cl. ........................ 435/7.1; 422/55; 422/56; 422/57; 422/61; 435/7.9; 435/7.91; 435/7.92; 435/7.93; 435/7.94; 435/287.1; 435/287.2; 435/287.7; 435/287.8; 435/287.9; 435/805; 435/810; 435/970; 435/973; 436/169; 436/172; 436/514; 436/518; 436/524; 436/525; 436/805; 436/810
(58) Field of Search ................................ 422/55–58, 61; 435/7.9, 7.91, 7.92, 7.93, 7.94, 287.1, 287.2, 287.7, 287.8, 287.9, 805, 810, 970, 973; 436/514, 518, 519, 525, 169, 172, 805, 810

(56) References Cited

U.S. PATENT DOCUMENTS 4,313,734  2/1982  Leuvering .
4,366,241  12/1982  Tom .

(List continued on next page.)

FOREIGN PATENT DOCUMENTS 0362809   4/1990  (EP) .
WO 89/05978  6/1989  (WO) .

OTHER PUBLICATIONS

Lou, S. C., et al., "One–Step Competitive Immunochromatographic Assay for Semiquantitative Determination of Lipoprotein(a) in Plasma," CLIN. CHEM. 39(4) :619–624 (1993).

Primary Examiner—Christopher L. Chin
(74) Attorney, Agent, or Firm—Klarquist Sparkman Campbell Leigh & Whinston, LLP

(57) ABSTRACT

Lateral flow device and method are provided for performing semi-quantitative visual or instrument-based detection in a test sample of a large molecule analyte that contains two binding domains, α and β. The device contains two reagents, a contrast reagent and an indicator reagent, and an analyte test zone (ATZ) that contains a fixed number of immobilized α-domain-specific binding sites. The contrast and indicator reagents each contain signal generators such that the two reagents contrast each other in different regions of a visual, spectrophotometric, calorimetric or fluorometric spectrum. The contrast reagent is prebound to an α-region-fragment of the analyte of interest and, therefore, does not react with the analyte of interest in the test sample. The indicator reagent is attached to a binding ligand specific for the β-domain of the analyte of interest. When a test sample is applied to the device, the analyte, if present, reacts with the indicator reagent and competes with the contrast reagent for the ATZ's α-domain binding sites. The analyte concentration in the test sample is evaluated by comparing the ratio of contrast and indicator signals in the ATZ with signal ratios for known analyte concentrations.

10 Claims, 5 Drawing Sheets

U.S. PATENT DOCUMENTS

| | | |
|---|---|---|
| 4,425,438 | 1/1984 | Bauman . |
| 4,703,017 | 10/1987 | Campbell . |
| 4,806,312 | 2/1989 | Greenquist . |
| 4,851,356 | 7/1989 | Canfield . |
| 4,861,711 | 8/1989 | Friesen . |
| 4,916,056 | 4/1990 | Brown . |
| 4,943,522 | 7/1990 | Eisinger . |
| 4,956,275 | 9/1990 | Zuk . |
| 4,959,305 | 9/1990 | Woodrum . |
| 4,963,468 | 10/1990 | Olson . |
| 4,981,786 | 1/1991 | Dafforn . |
| 4,999,285 | 3/1991 | Stiso . |
| 5,008,080 | 4/1991 | Brown . |
| 5,073,484 | 12/1991 | Swanson . |
| 5,075,078 | 12/1991 | Osikowicz . |
| 5,114,673 | 5/1992 | Berger . |
| 5,120,643 | 6/1992 | Ching . |
| 5,229,073 | 7/1993 | Luo . |
| 5,266,497 | 11/1993 | Imai . |
| 5,416,000 | 5/1995 | Allen . |
| 5,451,504 | 9/1995 | Fitzpatrick . |
| 5,591,645 | 1/1997 | Rosenstein . |
| 5,622,871 | 4/1997 | May . |
| 5,654,162 | 8/1997 | Guire . |
| 5,656,503 | 8/1997 | May . |

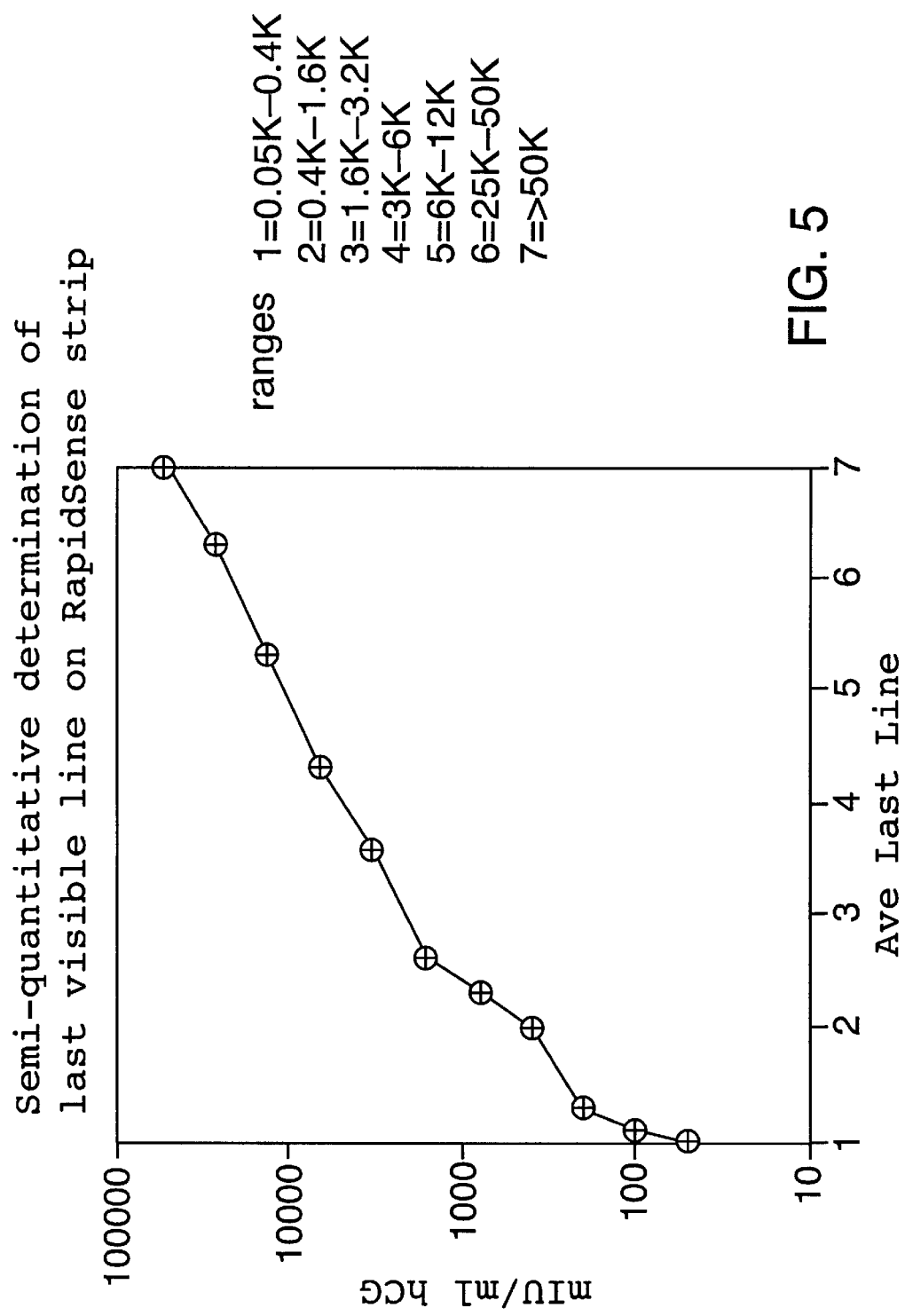

SINGLE OR MULTIPLE ANALYTE SEMI-QUANTITATIVE/QUANTITATIVE RAPID DIAGNOSTIC LATERAL FLOW TEST SYSTEM FOR LARGE MOLECULES

This application is based on and claims the benefit of U.S. Provisional Application No. 60/048,902, filed Jun. 5, 1997, and the contents thereof are incorporated herein by reference.

BACKGROUND OF THE INVENTION

1. Field of the Invention

The present invention relates generally to a diagnostic device and more specifically to a lateral flow assay device ("LFD") that provides quantitative or semi-quantitative results.

2. Background Information

Assays are needed and used for detecting the presence of analytes in liquid test samples in fields such as clinical and forensic medicine, environmental testing, food contaminant testing, and drug use testing. In particular demand are single step assays that are based on reactions between specifically reactive substances that can be conducted outside of the laboratory setting and in remote sites.

At present, there are a number of over-the-counter home testing and health care professional diagnostic devices that act to both collect human body fluids and perform a diagnostic assay. Some of these devices are used for midstream urine collection, while other devices involve dipstick collection of a fluid biological sample placed in a receptacle. Both types of diagnostic devices can employ a lateral flow technology with common features, including an absorbent wick, matrix and reaction zones.

Using such a device involves applying a biological or aqueous test sample to the matrix. The matrix usually is a porous carrier material. When the matrix does not have sufficient absorbent capacity, a wick is used to transfer the sample to the matrix. The test sample is applied to the wick or one end of the matrix strip and moves by capillary action in one direction along the matrix to a reaction zone.

The reaction zone contains a first reactant. The first reactant is usually diffusible conjugate formed from an antibody, or other ligand, and a marker substance. The first reactant is specifically selected to react with a component of interest in the test sample. The sample enters the reaction zone and the component of interest binds with the first reactant to form complexes.

The reactant complexes, any unreacted sample, and conjugate move by capillary action out of the reactant zone and into a single test capture zone. Within the test capture zone is a second reactant that is immobilized to the matrix. The reactant complexes that contain test capture zone binding sites are retained at the test capture site through the formation of a sandwich reaction product. Those reactant complexes that do not contain test capture binding sites move by capillary action out of the test capture zone, into a control capture zone where they are bound or continue to move along the matrix and out of the capture zones. The control capture zone usually contains an antibody that has a specificity for binding the conjugate.

LFD formats require a control indicator to insure that the test was performed properly. This indicator is a validity test, i.e., it shows whether enough sample has migrated past the test capture binding site and, therefore, that the test procedure is performing properly.

Two formats exist for test and control zones on LFDs. In the format used in the overwhelming majority of LFDs, each zone forms a line across the matrix strip. The first line (i.e., the line first touched by the sample's fluid front after moving through the reaction zone) is the test line. Parallel and adjacent to the test line is the control line. The second format, a +/− indicator system, is present in a few formats (see U.S. Pat. Nos. 4,916,056, 5,008,080 and 5,075,078). Several other indicator configurations, including dots, curved lines and triangles, are possible but have not received wide commercial use.

Using existing lateral flow devices, test results are based on the visual detection of a threshold using a single color for the test result indicator. The test results are determined in one of two methods. In one method, the test results are determined from the total number of discrete lines or bands containing the indicator color (see e.g., U.S. Pat. Nos. 4,425,438, 5,073,484, 5,229,073 and 5,451,504). In the alternative method, the test results are determined from the migration distance of a continuous color front (see e.g., U.S. Pat. No. 5,416,000). Discriminating the last line or band or where the color front ends is difficult in these methods and results in uncertainty. The uncertainty in determining the last line/band or the end of the color front is due to the lack of competition for unbound immobilized binding sites and lot-to-lot manufacturing variability in the number of immobilized binding sites present on the device. Thus, a need exits for a lateral flow device that provides accurate, reproducible, semi-quantitative results with a single line or region independent of the number of binding sites present. The present invention satisfies this need and provides related advantages as well.

SUMMARY OF THE INVENTION

The present invention provides a sandwich format LFD with a single test line that is compatible with semi-quantitative detection of large molecule analytes (molecular weight is greater than 3,000 daltons) at low concentrations. Marker competition for binding sites at the single test line within an analyte test zone (ATZ) will indicate zero, low or high concentrations of the analyte of interest.

In accordance with one embodiment of the present invention, a sandwich format LFD with multiple test lines within the ATZ allows for titration of the analyte concentration and semi-quantitative detection.

In another aspect of the present invention, an analyte capture zone referred to as an analyte modulating zone (AMZ) is included in a location reached by the sample prior to reaching the ATZ. The AMZ alters performance by removing a fraction of the analyte and, thereby, increases the detectable range of analyte concentration.

In another aspect of the present invention, an LFD is provided in which a differential amount of immobilized binding ligand in a specified gradient among the multiple test lines is used to modulate the range of concentrations of analyte competing for the limited number of binding sites on the test line. This modulation allows the LFD to accommodate a particular range of concentrations according to the specification of the test.

BRIEF DESCRIPTION OF THE DRAWINGS

FIG. 5 is a graphical representation of the average last line seen visually in the multiple line format (depicted in FIG. 2) for increasing concentrations of hCG.

DETAILED DESCRIPTION OF THE INVENTION

The invention provides improved immunological and other specific binding assay methods and devices in a single or multi-analyte format, using contrast or control and indicator reagents in an LFD to instrumental or non-instrumental visual endpoints.

Sandwich LFD With Single Test Line

Figure 1:
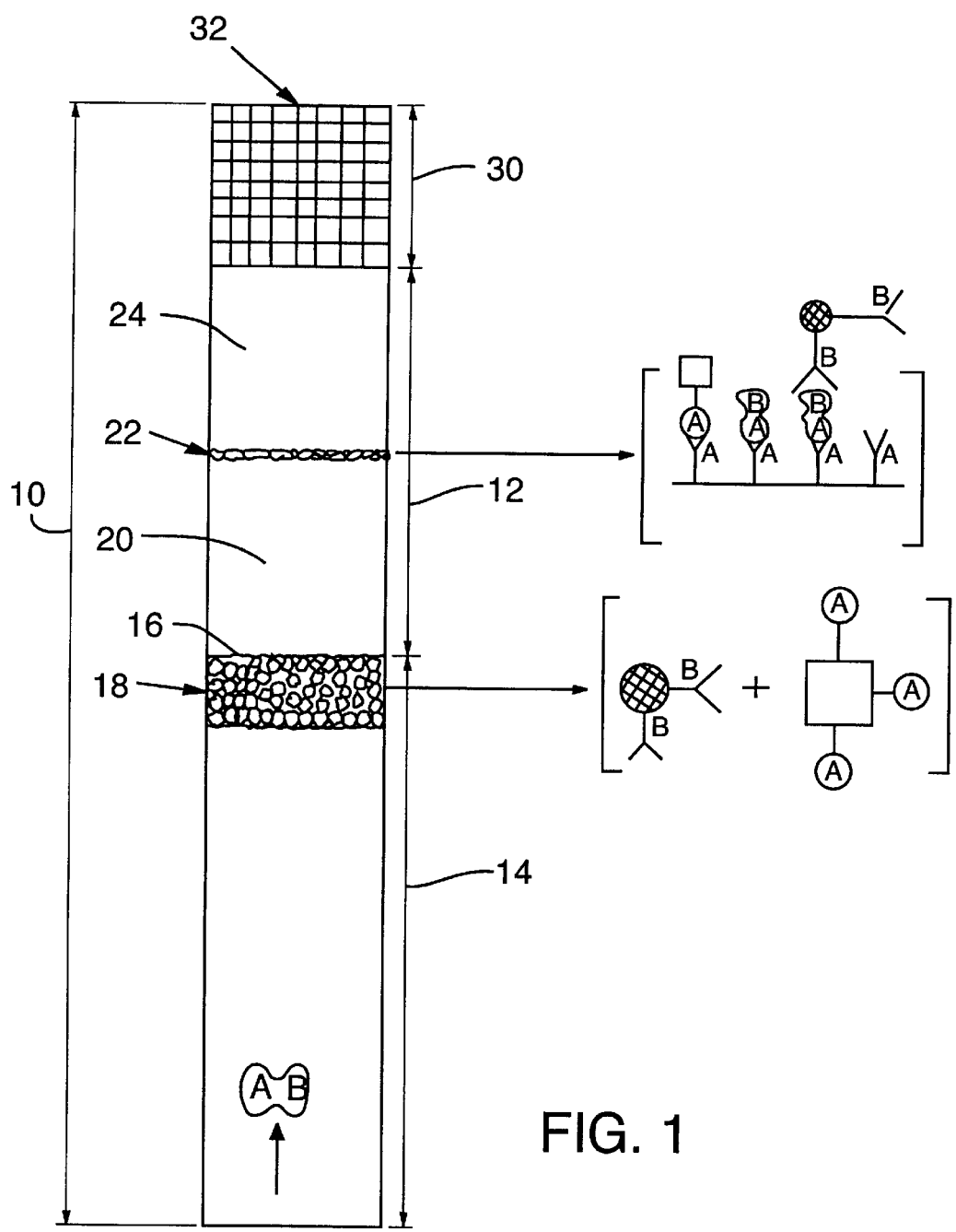
FIG. 1 is a schematic representation of a sandwich format LFD with a single test line that is compatible with semi-quantitative detection of large molecule analytes.

A sandwich format lateral flow device ("LFD") with a single test line for the determination and semi-quantitative detection of a large molecule analyte in a biological or aqueous test sample is illustrated in FIG. 1. The various dimensions are not necessarily drawn to scale in any of the Figures.

The LFD 10 includes a porous membrane 12 made, for example, of nitrocellulose, glass fiber, or nylon. Other appropriate membrane materials can be used depending on the characteristics of pore size, binding capacity, the particular biological or aqueous test sample and assay procedure. Usually, the porous membrane 12 can have a pore size between 2 and 10 microns. In one form, the porous membrane 12 will have a length between approximately 50–100 mm and a width between approximately 3.5–8.0 mm. The porous membrane 12 also will have a thickness, for example, between approximately 50–300 microns and a capillary rise characteristic, relative to an aqueous solution, between approximately 10–50 mm/min. However, the specific characteristics and dimensions of the porous membrane 12 are not critical and can be modified as necessary to achieve desired results of speed and a positive test result.

As shown in FIG. 1, a wicking pad 14 overlaps the porous membrane 12 at one end 16 of membrane 12 such that it is in liquid transfer contact with the porous membrane 12. The wicking pad 14 can be made of glass fiber, fibrous cellulose or other suitable materials. The dimensions of the wicking pad 14, although usually not critical, can be, for example, between 20–50 mm in length, between 3.5–8 mm in width and 0.5–2.0 mm in thickness.

The LFD 10 includes a conjugate zone 18. The conjugate zone 18 can be a region of the wicking pad 14 or the porous membrane 12 or one or more separate reagent pads that are in liquid transfer contact with the wicking pad 14 or porous membrane 12. The wicking pad 14, porous membrane 12 and conjugate zone 18 can be held in place by a strip of tape (not shown). In other embodiments, the wicking pad 14, porous membrane 12 and conjugate zone 18 can be held in place by an adhesive material or by the natural constriction of a container (not shown) housing the LFD components and preventing their contamination.

The conjugate zone 18 contains two reagents. The first reagent is a contrast reagent that is attached to a portion or fragment of the large molecule analyte of interest (referred to herein as the "α-region-fragment") by covalent or ionic binding, adsorption or other means of attachment known in the art to form a contrast binding ligand (CL). The CL can be dried, reconstitutable, liquid-dispersible, diffusible, colored-latex beads. Usually, the latex beads are light in color; for example, yellow. Instead of colored-latex beads, the contrast reagent can be a colored dye molecule, an enzyme and dye combination, or a fluorescent, luminescent or radioactive molecule.

The second reagent contained in the conjugate zone 18 is a dried, reconstitutable, liquid dispersible, diffusible indicator reagent that is attached to a binding ligand specific for a second region ("β-region") of the large molecule analyte of interest to form an indicator binding ligand (IL). The α-region-fragment and β-region of the large molecule analyte must be separate non-cross-reacting units. The indicator reagent can be colloidal gold particles, enzyme/dye combinations, colored latex particles, carbon particles, or fluorescent, luminescent or radioactive particles that can be visibly or otherwise distinguished from the CL.

One or both of the first and second reagents can be uniformly impregnated or dispersed within the conjugate zone 18 before they are contacted by the test sample. Alternatively, for example, the conjugate zone 18 can be coated with one or both reagents and the reagents dispersed throughout the conjugate zone when contacted by the sample. Or the two reagents can be longitudinally spaced apart within the conjugate zone 18 and dispersed throughout the conjugate zone when contacted by the sample.

As shown in FIG. 1, the LFD 10 includes an absorption pad 30 at the second end 32 of the porous membrane 12 opposite the wicking pad 14. Between the absorption pad 30 and the conjugate zone 18 are one test line 22, a space 20 between the conjugate zone 18 and the test line 22, and a second space 24 between the test line 22 and absorption pad 30. The test line 22 is located on the porous membrane 12 and contains an immobilized binding ligand specific for the α-region-fragment of the analyte of interest.

The absorption pad 30 can be a glass fiber or fibrous cellulose pad or other suitable material in liquid transfer contact with the porous membrane 12. The absorption pad 30 collects unreacted reagent and sample and acts as a wick to remove any background material from the test line 22.

A test sample containing an analyte moves along the wicking pad 14, shown in FIG. 1, to the conjugate zone 18 by capillary action. When the sample comes into contact with the IL in the conjugate zone 18, it reacts to form an analyte-IL complex. The CL attached to the α-region-fragments moves along the wicking pad with, but does not react with, the analyte or the analyte-IL complex.

When the test sample's fluid front reaches the test line 22, a competition for the immobilized α-region-specific ligand's binding sites occurs among the CL, analyte-IL complexes, and uncomplexed analyte. For purposes of illustration only, for the following example the contrast reagent is yellow latex beads and the indicator reagent is colloidal gold particles. When no analyte is present in the test sample, only α-region-fragments-yellow latex beads (CL) will attach to the α-region-fragment-specific ligands immobilized on test line 22 and test line 22 will appear yellow. When there is a small concentration of analyte in the sample, the CL and IL will compete for the limited number of binding sites on the α-region-fragment-specific ligand immobilized on the test line 22, with the yellow-colored beads predominating over the red of the colloidal gold complex forming a brown color. As the concentration of analyte increases, the concentrations of analyte-IL complexes increases and competes more effectively for the limited number of α-region-fragment-specific ligand binding sites, and the test line 22 will become more red in color.

The above-described transition in color in the test line 22 from yellow to brown to red forms the basis of a semi-quantitative single line test. Comparable transitions can be achieved by substituting other contrast and indicator reagents for the latex beads and colloidal gold. In each case, a visual or otherwise detectable test line 22, or color or signal transition pattern for multiple regions, will develop whether the test is negative or positive and will serve as a procedural control for test validity.

After moving into the test line 22, any unbound sample constituents and reagents continue to move up the porous membrane 12 into the absorption pad 30, which acts as a wick to pull sample upward, thus washing out the test line 22 area of any background material.

Sandwich LFD With AMZ

For analytes that occur in high concentrations, the range over which the analyte is determined can be increased by preparing an AMZ that intercepts a portion of the analyte prior to the sample reaching the test line 22 in FIG. 1. A capture antibody or other capture molecule can be attached to the wicking pad 14 or, for example, in space 20 on porous membrane 12 by known methods. The capture molecule lowers the concentration of analyte in a test sample by removing a fraction of the analyte and, thereby, extends the range of the color or other signal transition zone detected at test line 22. The fraction of the analyte removed in the AMZ can be empirically established during manufacturing and quality control procedures for the LFD 10 and specific analyte.

The AMZ is described in greater detail in Example I for a sandwich LFD with a single test line, where an AMZ has extended the range of the test. The AMZ also can be used and applied to other sandwich LFD formats.

Sandwich LFD With Reference Line

Figure 3:
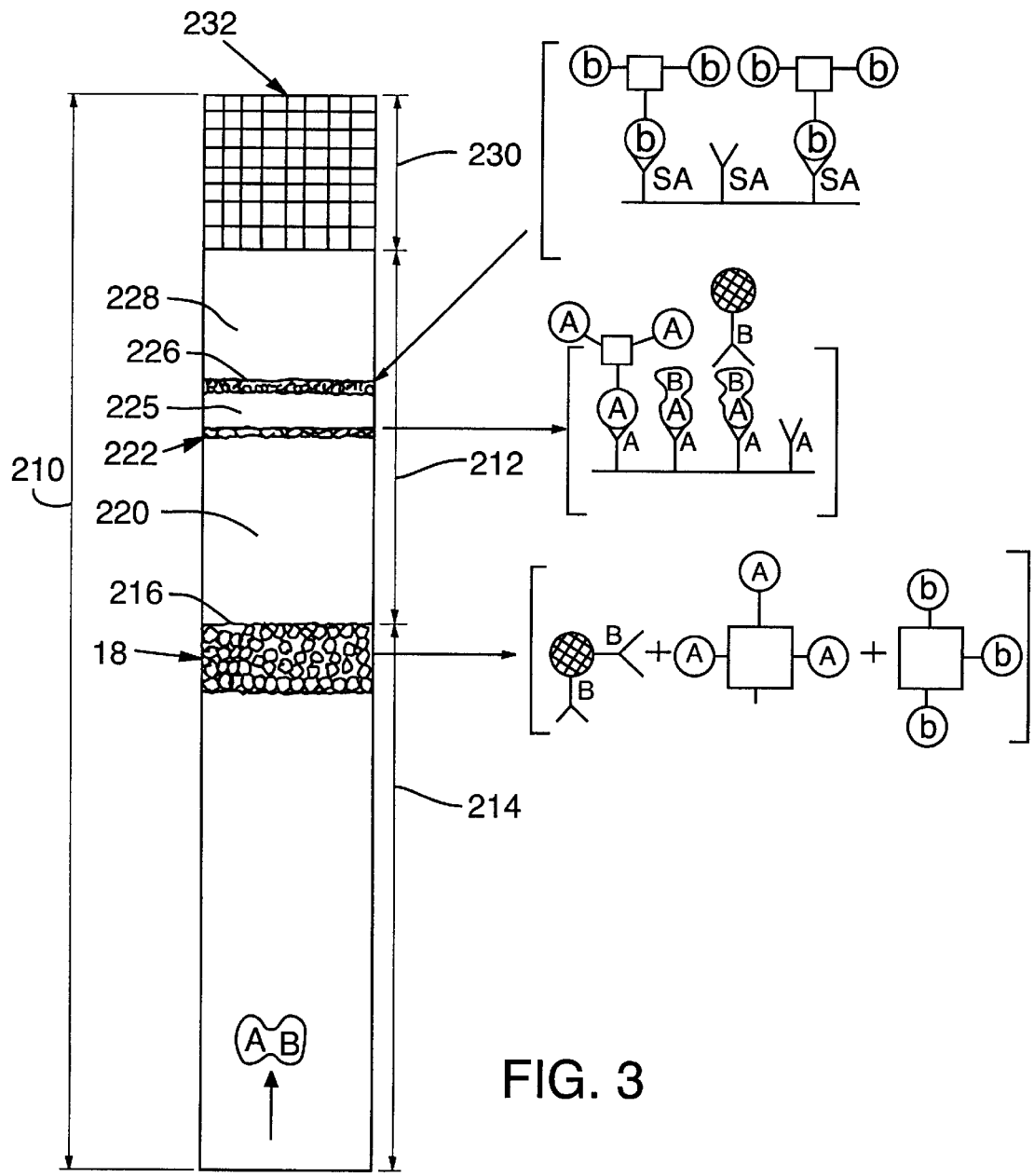
FIG. 3 is a schematic representation of an alternative embodiment of a sandwich format LFD that includes a reference line.

The sandwich format LFD 10 of FIG. 1 also can be modified to accommodate a reference line 226 as shown in FIG. 3. Functionally, the reference line 226 provides a check for samples containing very low amounts of analyte.

Structurally, the LFD 210 of FIG. 3 differs for the LFD 10 for FIG. 1 in the following ways. There are two separate species of contrast reagents used in the conjugate zone 218. The first species is the CL of the analyte of interest described above for FIG. 1. The second species is created by attaching the contrast reagent to a capturable label that has a specific capturing binding partner. One example of such a capturable label and capturing binding partner is biotin and streptavidin. Other suitable labels and binding partners are known in the art and can be incorporated by standard methods.

The capturing binding partner is immobilized on the porous membrane 212 to form a reference line 226. The reference line 226 is located at the second end 232 of the porous membrane 212 between the conjugate zone 218 and the absorption pad 230. The reference line 226 usually is distanced from the conjugate zone 218 by approximately 2–4 mm and absorption pad 230 by approximately 5–50 mm to create a first space 224 and second space 228 on the porous membrane 212.

When the sample moves up the porous membrane 212 from the conjugate zone 218, the contrast reagents will travel with it. The contrast reagent attached to the α-region-fragment (CL) will compete for immobilized α-region-fragment-specific ligand binding sites on ATZ 222 with analyte-IL complexes as described for FIG. 1. The contrast reagent attached to the capturable label will bind to the capturing binding partner immobilized at the reference line 226.

For purposes of illustration only, for the following that contrast reagent is yellow latex beads and the indicator reagent is colloidal gold particles. If there is no analyte in the sample, the color of the reference line 226 and test line 222 will be the same color. When there is analyte in the sample, the reference line 226 will be yellow while the test line 222 will be brown to red in color, depending on the concentration of analyte in the sample. The color of the reference line 226 thus provides a basis for color comparison with the color of the test line 222. Comparable reference line and test line comparisons can be achieved with other contrast and indicator reagents.

Sandwich LFD With Multiple Test Regions

Figure 2:
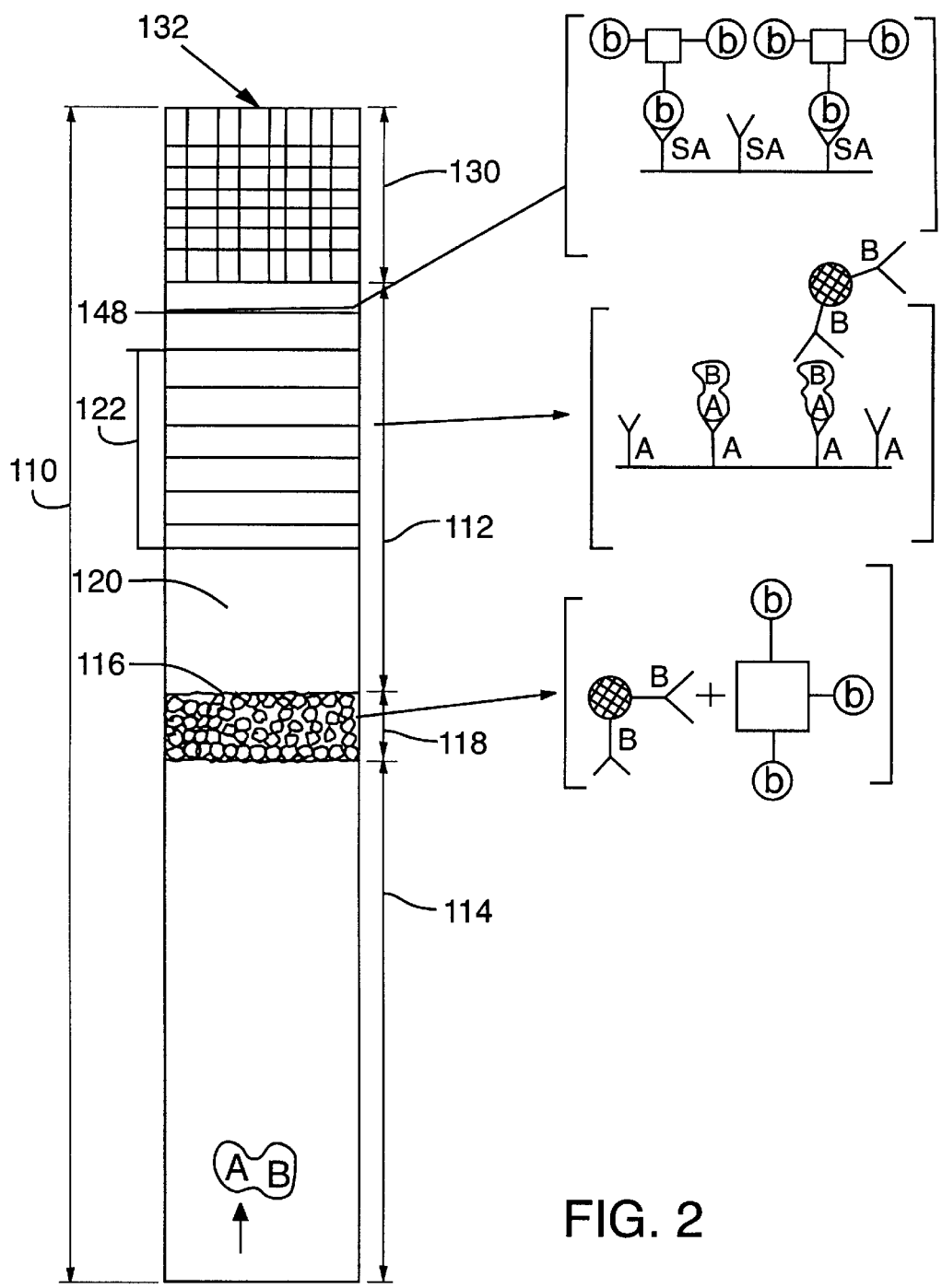
FIG. 2 is a schematic representation of a sandwich format LFD with multiple test lines that is compatible with semiquantitative detection of large molecule analytes. This particular format includes a control line.

A sandwich LFD format with multiple parallel test lines (regions) for the determination and titration of an immunologically reactive large molecule analyte in a test sample is illustrated in FIG. 2. This format enables the user to determine zero, from lower and higher concentrations of analyte, by the use of a scale to correlate the location of a color transition zone. The test lines that develop are detectable on the porous membrane due to binding of the analyte-IL complex to the limited number of immobilized binding sites on the ATZ.

Using multiple parallel test lines allows for a titration of the analyte concentration. Zero or subthreshold levels of analyte will not form lines within the matrix. Small amounts of IL will be completely captured by the first or second line. Larger amounts of analyte will be captured by subsequent lines as the analyte sequentially saturates the binding sites. The analyte, therefore, is quantitated by the color or signal transition pattern.

The LFD 110 includes a porous membrane 112 made of nitrocellulose, glass fiber, nylon or other suitable materials. The specific dimensions of the porous membrane 112 are not critical and maybe modified as necessary to achieve desired results of speed and positive test results.

As shown in FIG. 2, a wicking pad 114 overlaps the porous membrane 112 at one end 116 of membrane 112 such that it is in liquid transfer contact with the porous membrane 112. The wicking pad 114 can be made of glass fiber, fibrous cellulose or other suitable materials.

The LFD 110 includes a conjugate zone 118. In FIG. 2, as in FIG. 1, the conjugate zone 118 can be either a region of the wicking pad 114 or porous membrane 112 or one or more separate reagent pads in liquid transfer contact with the wicking pad 118 or porous membrane 112. The wicking pad 114, porous membrane 112 and conjugate zone 118 can be held in place by a variety of methods known in the art.

The conjugate zone 118 contains two reagents. The first reagent is a labeled control reagent. It, for example, can be dried, colored, liquid dispersible, diffusible latex beads. The label is one that has a specific binding partner, e.g., biotin and streptavidin. The beads are usually light in color; for example, yellow. As an alternative to colored-latex beads, the control reagent may be a light-colored dye molecule, an enzyme and dye combination, or a fluorescent, luminescent or radioactive molecule.

The second reagent contained in the conjugate zone 118, is a dried, reconstitutable, liquid dispersible, diffusible indicator reagent that is attached to a binding ligand specific for a region ("β-region") of the large molecule analyte of interest to form an indicator binding ligand (IL). The indicator reagent can be colloidal gold particles, enzyme/dye combinations, colored latex particles, carbon particles, or fluorescent, luminescent or radioactive molecules that can be visibly or otherwise distinguished from the control reagent.

One or both of the first and second reagents can be uniformly impregnated or dispersed within the conjugate zone 118 before they are contacted by the test sample. Alternatively, for example, the conjugate zone 118 can be coated with one or both reagents and the reagents dispersed throughout the conjugate zone when contacted by the sample. Or the two reagents can be longitudinally spaced apart within the conjugate zone 118 and dispersed throughout the conjugate zone when contacted by the sample.

As shown in FIG. 2, the LFD 110 includes between 2 and 20, usually about 7, multiple test lines 122, a space 120 between the conjugate zone 118 and the test lines 122, and a space 124 between the test lines 122 and an absorption pad 130 at the second end 132 of the porous membrane 112. The test lines 122 contain a binding ligand specific for a second region ($\alpha$-region) of the analyte of interest that is immobilized on the porous membrane 112. The $\alpha$- and $\beta$-regions of the large molecule analyte must be separate non-cross-reacting units.

A control line 148 is located on the porous membrane 112 near end 132. The control line 148 contains an immobilized binding partner (e.g., streptavidin) for the label attached to the control reagent (e.g., biotin).

The absorption pad 130 can be glass fiber, fibrous cellulose or other suitable material in liquid transfer contact with the porous membrane 112. The absorption pad 130 collects unreacted reagent and sample constituents and acts as a wick to remove any background material from the test lines 122.

A test sample containing an analyte moves along the wicking pad 114 of FIG. 2 to the conjugate zone 118 by capillary action. When the sample comes into contact with the IL in the conjugate zone 118, it reacts to form an analyte-IL complex. The labeled control reagent moves along the wicking pad 114 with, but does not react with, the analyte-IL complex or IL. When the sample's fluid front reaches the test lines 122, only the analyte-IL complex and any uncomplexed analyte will bind to the $\alpha$-region-specific ligand immobilized on test lines 122.

For purposes of illustration only, for the following the control reagent is yellow latex beads and the indicator reagent is colloidal gold particles. When there is no analyte, no test lines have color or are otherwise visible. As the concentration of analyte increases in the test sample, the concentration of analyte-IL complexes increases and saturates the limited number of $\alpha$-region-specific ligand binding sites at test lines 122, creating a situation where more of the test lines 122 will become red in color.

The labeled yellow-colored latex beads will continue to migrate and then react with the label's binding partner immobilized on control line 148. The control line 148 will be colored both in the presence and absence of analyte. The color of the control line 148 will be distinct from the test lines 122. After moving through the test lines 122 and control lines 148, the sample continues to move up the porous membrane 112 onto the absorption pad 130 which collects unreacted reagents and sample and acts as a wick to remove from the test line area 122 any background material.

Examples of the above described LFDs used to detect hCG in urine samples are found in Examples I, II, and III below. Other large molecule analytes of interest include drugs, hormones, synthetic chemicals, pollutants, trace compounds, toxins and microorganisms in biological fluids, food, water or air. Additional detection analytes that are either present in fluids or can be introduced into a liquid system and appropriate reagents will be known to those of skill in the art.

Multiple test lines in the ATZ (as shown in FIG. 2, area 122) could be used in the format of FIGS. 1 and 3 and the resulting color or signal transition pattern in the ATZ is then compared with that of patterns from known analyte concentrations.

Devices described herein can include more than one IL, wherein each IL has different and spectrally non-overlapping visual, spectrophotometric, colorimetric or fluorometric properties.

EXAMPLE I

SANDWICH LFD WITH SINGLE TEST LINE

Preparation of Test Strips

Pregnancy test strips (SA Scientific, San Antonio, Tex.) containing dried anti-$\beta$ hCG monoclonal antibody conjugated to colloidal gold on a glass fiber conjugate pad were obtained. These strips contained immobilized anti-$\alpha$ hCG on a test line and immobilized anti-mouse IgG on a control line on a nitrocellulose membrane similar to what is depicted in FIG. 1. The conjugate pad was carefully removed intact using a razor blade. To the region of nitrocellulose membrane corresponding to space 20 in FIG. 1, varying amounts of monoclonal anti-$\beta$ hCG capture antibody (0, 250, 500, 1000, 2000 ng) were added, dried, washed and dried again.

The conjugate pad was carefully and uniformly coated with a total of 3 ul (in 0.2 ul drops) of a 10 mg/ml solution of yellow latex beads (200 nm particles, carboxylated) covalently conjugated with affinity purified $\alpha$-region of hCG (20 ng/mg latex). The pad was then dried at 50° C. The conjugate pad was then placed back in its original position on the modified test strip and secured with cellophane tape.

Test Procedure

Negative urine samples were spiked with hCG to achieve concentrations of 0, 25, 225, 450, 1100, 2500, 10,000 and 100,000 mIU/ml. A 0.3 ml aliquot from each of the 8 spiked urine samples was added to separate microfuge tubes. The wicking pad of each test strip was placed in contact with the urine. Each strip contained a set amount of immobilized capture antibody and a conjugate pad as described above.

After five minutes, the ATZ on each test strip was then visually scored for color type as either yellow (Y), brown (B), red-brown (RB), or red (R). The test results are summarized in Table I.

The results in Table I show a semi-quantitative capability arising from the use of a yellow-colored latex and red colloidal gold combination. The results also show that there is an improvement in the range of concentrations indicated by the brown-colored line achieved by removing excess hCG at the higher immobilized anti-$\beta$ monoclonal antibody levels in the AMZ. The additional antibody did not compromise sensitivity, and there were no false positives due to non-specific binding of the colloidal gold to the test line. At 1000 and 2000 ng of anti-$\beta$ hCG capture antibody, the brown color extended to 1000 mIU/ml, which is 3–5 times higher than the range seen in the control, 0 ng, antibody strips.

EXAMPLE II

SANDWICH LFD WITH REFERENCE LINE

Preparation of Reference Line Test Strips

The preparation pregnancy strips (SA Scientific, San Antonio, Tex.) with reference lines containing immobilized streptavidin required temporary removal of the conjugated pads from the pregnancy strips to avoid damaging the pads during preparation of test strips corresponding to FIG. 3. While each conjugate pad was removed, a coating of 3 ul biotin-labeled yellow latex beads (10 mg/ml) and yellow latex beads covalently conjugated with α-region-fragments of hCG (10 mg/ml) were added to the reagent pad as described above in Example I.

The reference line 226 can be prepared by immobilizing streptavidin directly on the porous membrane using passive adsorption or other methods known in the art.

Test Procedure

Test procedures were identical to those in Example I, except that only 0, 25, and 10,000 mIU/ml samples were tested.

Test Results

In the negative sample, the yellow color in the test line 222 was indistinguishable from the reference line 226. The 25 mIU/ml sample displayed a weak brown color relative to the yellow reference line. The 10,000 mIU/ml sample yielded a solid red test line and a yellow reference line.

EXAMPLE III

SANDWICH LFD WITH MULTIPLE TEST LINE ATZ

Preparation of Test Strips

Custom test strips corresponding to FIG. 2 were prepared that contained 7 anti-α hCG antibody test lines spaced 1 mm apart on the nitrocellulose membrane. A line of streptavidin was immobilized on the control line 148 as described for the reference line 226 in Example II.

Yellow latex-BSA conjugated with biotin (3 ml at 10 mg/ml) was added to the anti-β hCG monoclonal antibody-colloidal gold treated conjugate pad and air dried. The pad was secured to the test strips with cellophane tape to the backing.

Seven test lines 122 were prepared as described for test lines 22 in Example I.

Test Procedure

Figure 4:
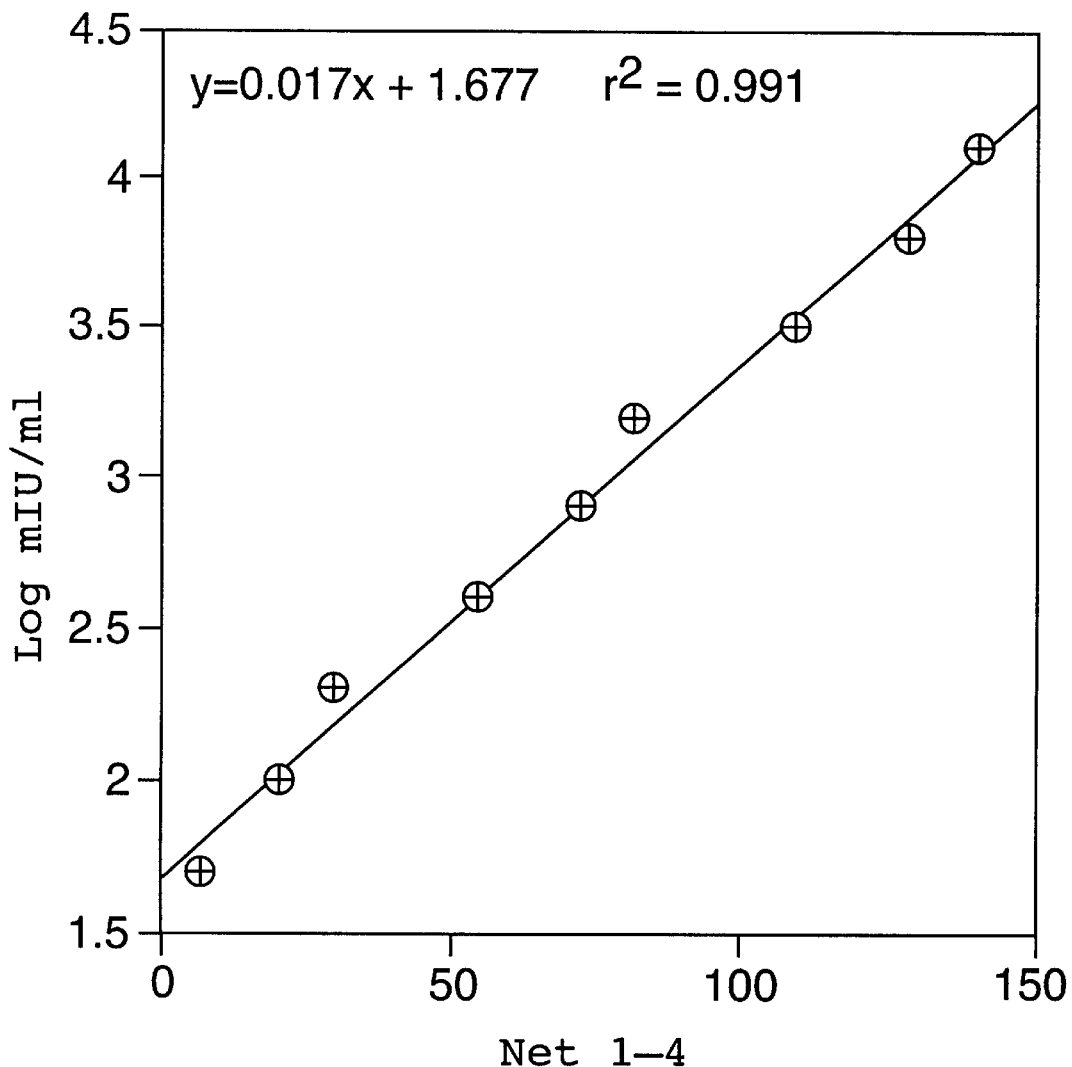
FIG. 4 is a graphical representation of a linear least squares fit of the average color intensity of the sum of lines 1–4 as measured on a Minolta CR-241 color analyzer of the multiple test line format (depicted in FIG. 2) for increasing concentrations of human chorionic gonadotropin(hCG).

The following procedure was performed in triplicate using the test strips prepared above. The strips were placed in 0.5 ml of hCG negative urine that had been spiked with varying amounts of hCG (0–51,200 mIU/ml). The strips were allowed to develop for 10 minutes. The strips were then dried for 2 hours, at 50° C. and color intensity determined on a colorimeter using the Yxy color field (Minolta CR-241, 0.3 discrimination aperture). The signal intensities were then calculated using the sum of the first four lines (net 1–4) for the Y color space. The data is presented in Table II. A plot was then made correlating the Net 1–4 with the log hCG concentration, shown in FIG. 4. A linear least squares fit was derived and values were calculated from that fit for each hCG concentration tested, and compared to the known values (Table III). A visual discrimination of the line number containing the last visible red line was also performed on the test strips developed above. The results were summarized in Table IV, and the averages were plotted in FIG. 5.

Test Results

The multi-test line format allows for quantitating the level of hCG in urine. Calculated values differed from known values on average by 13%, with a range of from 0.6–26.3%. A visual semi-quantitative method allows the user to place the hCG concentration into 5–7 ranges of hCG within a range of 50 mIU/ml to greater than 50,000 mIU/ml.

Although the invention has been described with reference to the examples provided above, it should be understood that various modifications can be made without departing from the spirit of the invention.

TABLE I

| mIU/ml hCG | anti-β hCG capture mAb immobilized | | | | |
|---|---|---|---|---|---|
| | 0 ng | 250 ng | 500 ng | 1000 ng | 2000 ng |
| 0 | Y | Y | Y | Y | Y |
| 25 | B | B | B | B | B |
| 225 | B | B | B | B | B |
| 450 | R | RB | RB | B | B |
| 1100 | R | RB | R | RB | RB |
| 2500 | R | R | R | R | R |
| 10,000 | R | R | R | R | R |
| 100,000 | R | R | R | R | R |

TABLE II

| strip | | 1 | 2 | 3 | 4 | 5 | 6 | 7 | 8 | 9 | 10 | 11 | 12 |
|---|---|---|---|---|---|---|---|---|---|---|---|---|---|
| line | | | | | | | | | | | | | |
| | 1 | 90.19 | 84.83 | 75.14 | 66.59 | 40.86 | 29.92 | 34.01 | 27.76 | 16.19 | 15.78 | 23.76 | 19.15 |
| | 1 | | 83.98 | 75.23 | 71.24 | 55.68 | 43.1 | 41.3 | 23.74 | 22.68 | 20.92 | 21.56 | 15.85 |
| | 1 | | 84.43 | 75.06 | 55.39 | 57.77 | 47.08 | 35.69 | 31.55 | 26.71 | 18.24 | 22.12 | 19.92 |
| 1 ave | | 90.19 | 84.41 | 75.143 | 64.41 | 51.44 | 40.03 | 37 | 27.68 | 21.86 | 18.313 | 22.48 | 18.31 |
| | 2 | 89.7 | 91.99 | 87.34 | 86.9 | 76.62 | 71.4 | 69.63 | 56.71 | 42.97 | 50.77 | 41.73 | 19.14 |
| | 2 | | 89.65 | 86.71 | 85.54 | 83.53 | 75.26 | 75.41 | 58.43 | 55.34 | 44.94 | 34.6 | 24.47 |
| | 2 | | 87.68 | 88.23 | 88.69 | 81.89 | 76.73 | 72.33 | 63.66 | 58.68 | 52.19 | 35.24 | 22.13 |
| 2 ave | | 89.7 | 89.77 | 87.427 | 87.04 | 80.68 | 74.46 | 72.46 | 59.6 | 52.33 | 49.3 | 38/10 | 21.91 |
| | 3 | 89.25 | 88.32 | 87.9 | 87.56 | 84.09 | 81.26 | 80.88 | 73.47 | 72.46 | 71.29 | 60.04 | 37.03 |
| | 3 | | 89.64 | 87.25 | 87.78 | 85.7 | 87.09 | 83.17 | 82.61 | 74.98 | 66.3 | 53.23 | 40.99 |
| | 3 | | 87.54 | 87.65 | 89.65 | 86.06 | 83.98 | 81.52 | 77.9 | 73.01 | 70.8 | 55.12 | 36.21 |
| 3 ave | | 89.25 | 88.5 | 87.6 | 88.33 | 85.28 | 84.11 | 81.86 | 77.99 | 73.48 | 69.463 | 56.13 | 38.08 |
| | 4 | 88.46 | 88.9 | 87.6 | 88.53 | 86.25 | 850.01 | 86.31 | 81.64 | 84.78 | 81.14 | 73.14 | 53.43 |
| | 4 | | 86.64 | 86.52 | 87.27 | 84.89 | 87.3 | 84.22 | 85.48 | 80.75 | 79.39 | 73.43 | 59.19 |
| | 4 | | | 87.25 | 89.26 | 87.17 | 87.45 | 85.29 | 83.88 | 80.74 | 81.08 | 72.94 | 61.02 |
| 4 ave | | 88.46 | 87.77 | 87.123 | 88.35 | 86.1 | 86.59 | 85.27 | 83.67 | 82.09 | 80.537 | 73.17 | 57.88 |
| Total | | 357.6 | 350.5 | 337.29 | 328.1 | 303.5 | 285.2 | 276.6 | 248.9 | 229.8 | 217.61 | 188.97 | 136.2 |
| Net 1–4 | | 0 | 7.143 | 20.307 | 29.47 | 54.1 | 72.41 | 81.01 | 108.7 | 127.8 | 139.99 | 168.63 | 221.4 |
| mIU/ml | | 1 | 50 | 100 | 200 | 400 | 800 | 1600 | 3200 | 6400 | 12800 | 25600 | 51200 |
| log mIU/ml | | 0 | 1.699 | 2 | 2.301 | 2.602 | 2.903 | 3.204 | 3.505 | 3,806 | 4.1072 | 4.4082 | 4.709 |

TABLE III

| mIU/ml hCG | Ave Line 1–4 net Y | Calculated mIU/ml | % difference |
|---|---|---|---|
| 50 | 7.1 | 61.5 | 23 |
| 100 | 20.3 | 104 | 4.2 |
| 200 | 29.2 | 150 | 24.7 |
| 400 | 54.1 | 402 | 0.6 |
| 800 | 72.4 | 836 | 4.5 |
| 1600 | 81 | 1179 | 26.3 |
| 3200 | 108.7 | 3569 | 11.5 |
| 6400 | 127.8 | 7659 | 19.7 |
| 12800 | 140 | 12474 | 2.5 |

TABLE IV

|  | Last line #1 | Last Line #2 | Last line #3 | Average |
|---|---|---|---|---|
| 50 | 1 | 1 | 1 | 1 |
| 100 | 1 | 1 | 1 | 1 |
| 200 | 1 | 2 | 1 | 1.3 |
| 400 | 2 | 2 | 2 | 2 |
| 800 | 3 | 2 | 2 | 2.3 |
| 1600 | 3 | 2 | 3 | 2.6 |
| 3200 | 4 | 3 | 3 | 3.6 |
| 6400 | 4 | 4 | 5 | 4.3 |
| 12800 | 6 | 5 | 5 | 5.3 |
| 25600 | 6 | 6 | 7 | 6.3 |
| 51200 | 7 | 7 | 7 | 7 |

What is claimed is:

1. A device for the quantitative or semi-quantitative determination of an analyte in a biological sample using a lateral flow device, said analyte containing two binding domains, α and β, said device comprising:
   a pad comprising an indicator binding ligand (IL) and a contrast binding ligand (CL),
      wherein said IL comprises an indicator signal generator that has visual, spectrophotometric, colorimetric or fluorometric properties and said IL has immobilized on its surface a binding ligand specific for the β-domain of the analyte; and
      wherein said CL comprises a contrast signal generator that has visual, spectrophotometric, calorimetric or fluorometric properties that contrast in different regions of the spectrum from the IL and said CL has immobilized on its surface a molecule that shares a binding determinant with the α-domain of the analyte;
   a porous membrane in liquid transfer contact with said pad,
      wherein said sample, IL and CL are capable of diffusing through said porous membrane by capillary action; and
   an analyte test zone (ATZ) on said porous membrane, wherein said ATZ comprises a fixed limited number of immobilized α-domain-specific binding sites.

2. The device of claim 1, further comprising an absorption pad in liquid transfer contact with the porous membrane.

3. The device of claim 1, wherein said IL and CL are dried and integrated into said pad until said sample solubilizes and mobilizes said IL and CL.

4. The device of claim 1, wherein the indicator signal generator is selected from the group consisting of a colloidal metal particle, a colored latex particle, a enzyme/colored dye substrate system, a carbon particle, a fluorescent particle, a luminescent particle and a radioactive particle.

5. The device of claim 1, wherein the contrast signal generator is selected from the group consisting of a colored latex particle, a colored dye molecule, an enzyme/colored dye substrate system, a fluorescent molecule, a luminescent molecule and a radioactive molecule.

6. The device of claim 1, further comprising at least one additional IL, each additional IL having different and spectrally non-overlapping visual, spectrophotometric, calorimetric or fluorometric properties.

7. The device of claim 1 further comprising:
   an analyte modulating zone (AMZ) consisting of one or more sequentially arranged capture regions immobilized on said porous membrane located between said pad and said ATZ, said AMZ capture regions containing a pre-determined amount of analyte binding capacity and reducing the amount of analyte reaching the ATZ at a level determined by the amount of analyte binding capacity in said AMZ capture regions.

8. The device of claim 1, wherein said ATZ consists of one or more sequentially arranged capture regions immobilized on a porous membrane or other liquid permeable surface having a pre-determined amount of analyte binding capacity and immobilizes the analyte and analyte-IL complexes to form detectable indicator regions whose signal pattern reflect differences in concentrations of the analyte.

9. Method of claim 1, wherein said ATZ contains binding sites in one or more separate test regions.

10. A device for the quantitative or semi-quantitative determination of an analyte, said analyte containing two binding domains, α and β, said device comprising:
   contacting means for contacting said device's pad with a test sample potentially containing said analyte;
   mixing means in liquid transfer contact with said contacting means, for allowing mixing of said sample with an indicator binding ligand (IL) and said CL;
   reaction means in liquid transfer contact with said mixing means, for allowing reaction of said IL with said analyte present in said sample to form an analyte-IL complex;
   migration means in liquid transfer contact with said reaction means, for allowing migration of said IL, IL-analyte complex, and CL along said porous membrane to said ATZ;
   competitive binding means in liquid transfer contact with said migration means, for allowing competitive binding of said IL, IL-analyte, and CL to said ATZ in proportions that are directly related to the concentration of analyte; and
   evaluating means in visual, spectrophotometric, calorimetric or fluorometric contact with said competitive binding means, for evaluating said ATZ for analyte concentration by comparing said ATZ visual, spectrophotometric, colorimetric or fluorometric transition signal pattern with that of known analyte concentrations.

* * * * *

UNITED STATES PATENT AND TRADEMARK OFFICE
CERTIFICATE OF CORRECTION

PATENT NO. : 6,258,548 B1
DATED : July 10, 2001
INVENTOR(S) : Robert L. Buck

Page 1 of 1

It is certified that error appears in the above-identified patent and that said Letters Patent is hereby corrected as shown below:

<u>Title page,</u>
ABSTRACT, line 10, "calorimetric" should read -- colorimetric --.

<u>Column 11,</u>
Line 41, "calorimetric" should read -- colorimetric --.

<u>Column 12,</u>
Lines 10-11, "calorimetric" should read -- colorimetric --.
Lines 55-56, "calorimetric" should read -- colorimetric --.

Signed and Sealed this

Twenty-first Day of May, 2002

*Attest:*

*Attesting Officer*

JAMES E. ROGAN
*Director of the United States Patent and Trademark Office*